Figure 1:
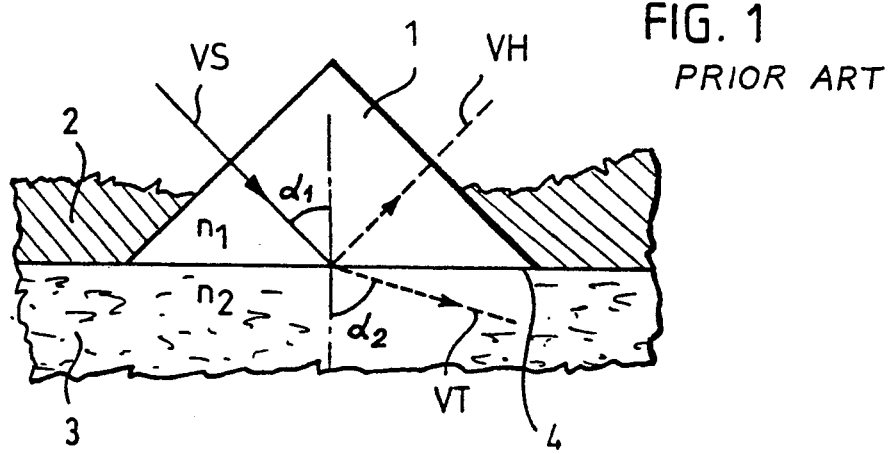

United States Patent [19]

Kahre

[11] Patent Number: 5,309,288

[45] Date of Patent: May 3, 1994

[54] PRISMATIC DEVICE FOR USE WITH PROCESS REFRACTOMETERS

[75] Inventor: Jan Kahre, Helsinki, Finland

[73] Assignee: Janesko Oy, Vantaa, Finland

[21] Appl. No.: 940,015

[22] Filed: Sep. 3, 1992

[30] Foreign Application Priority Data

Sep. 18, 1991 [FI] Finland ................................ 914386

[51] Int. Cl.$^5$ ......................... G02B 5/04; G01N 21/41
[52] U.S. Cl. ..................... 359/831; 359/837; 356/136
[58] Field of Search ............... 359/831, 833, 836, 837, 359/514; 356/136, 135; 385/36

[56] References Cited

U.S. PATENT DOCUMENTS

| | | | |
|---|---|---|---|
| 2,815,695 | 12/1957 | Scharf et al. | 359/583 |
| 3,883,214 | 3/1975 | Hoffman | 359/355 |
| 3,883,221 | 5/1975 | Rigrod | 385/36 |
| 4,119,980 | 10/1978 | Baker | 354/150 |
| 4,451,147 | 5/1984 | Dobes et al. | 356/135 |
| 4,485,405 | 11/1984 | Bailey | 359/222 |
| 4,634,223 | 1/1907 | Ishii | 359/834 |
| 4,699,516 | 10/1987 | Bartz et al. | 356/136 |
| 4,860,182 | 8/1989 | Vadseth | 362/364 |
| 4,910,403 | 3/1990 | Kilham et al. | 250/343 |
| 5,018,835 | 5/1991 | Dorschner | 359/87 |

FOREIGN PATENT DOCUMENTS

0359167A3  9/1989  European Pat. Off. .

*Primary Examiner*—Jon W. Henry
*Attorney, Agent, or Firm*—Fitch, Even, Tabin & Flannery

[57] ABSTRACT

A prism providing an optical window for a process refractometer. The prism is manufactured from a material that has predetermined optical properties and a refractory index higher than the refractory index of the process material to be measured. One face of the prism is arranged to provide an interface in contact with the process material to be measured. To optimise the selection of the material of the prism, an optically transparent material layer is provided onto the surface of the interface in contact with the process material, the refractory index of the material layer being higher than the refractory index of the material that the prism is manufactured from.

6 Claims, 1 Drawing Sheet

PRISMATIC DEVICE FOR USE WITH PROCESS REFRACTOMETERS

The invention pertains to a prism, more particularly to a prism providing an optical window for a process refractometer, the prism being manufactured from a material having predetermined optical properties and a refractive index higher than the refractive index of the process material to be measured, one face of the prism being arranged to provide an interface in contact with the process material to be measured.

Prisms of this kind are nowadays well known in connection with process refractometers utilised in different fields of technology. Process refractometers are now used, for example, in food industry, cellulose and paper industry, chemical industry, and in different research projects. An example for process refractometers known in the field is Process Refractometer PR-01 manufactured by K-Patents Oy and used for concentration measurement in the above technical fields.

In refractometers previously known in the field a prism providing an optical window in contact with the process material to be measured always consists of a single material. In practice it has been necessary to compromise on the material that the prism is manufactured from since it has not been possible to select the optically best material for the measuring of some substances because e.g. the wear resistance of the material concerned has not met the requirements set. Consequently, the measurement result is not optimal.

The object of the invention is to provide a prism by means of which the disadvantages of the previously known techniques can be eliminated. This is achieved with the aid of a prism according to the invention which is characterised in that onto the surface of the interface in contact with the process material is provided an optically transparent material layer, the refractory index of the material being higher than the refractory index of the material that the prism is manufactured from.

The main advantage of the prism according to the invention is that the material that the prism is manufactured from can be selected freely on optical criteria, i.e. in each case a material that is optically the best in the case concerned can be selected as the material of the prism. Thereby an optimal measurement result is obtained. A further advantage of the invention is that the need to clean the optical window decreases since the interface can be coated with a material that is not only wear resistant but also such that impurities do not adhere thereto and in addition its surface friction is small. Another advantage of the invention is its simplicity, whereby it is advantageous to utilise the invention.

Figure 2:
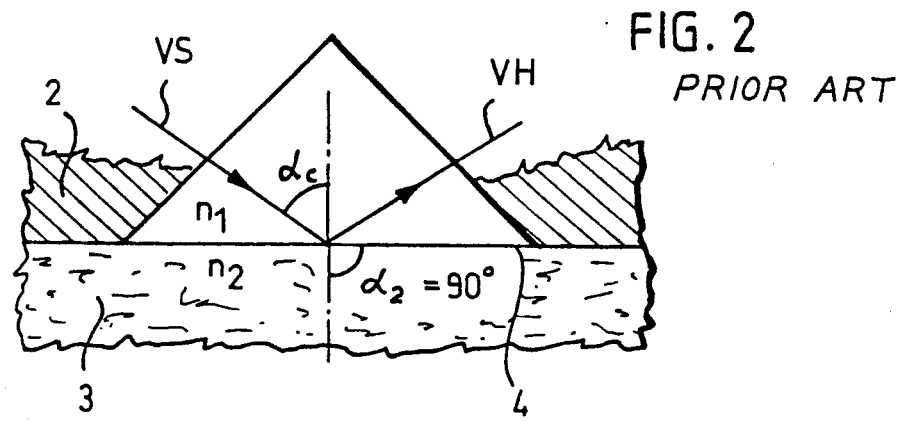
Figure 3:
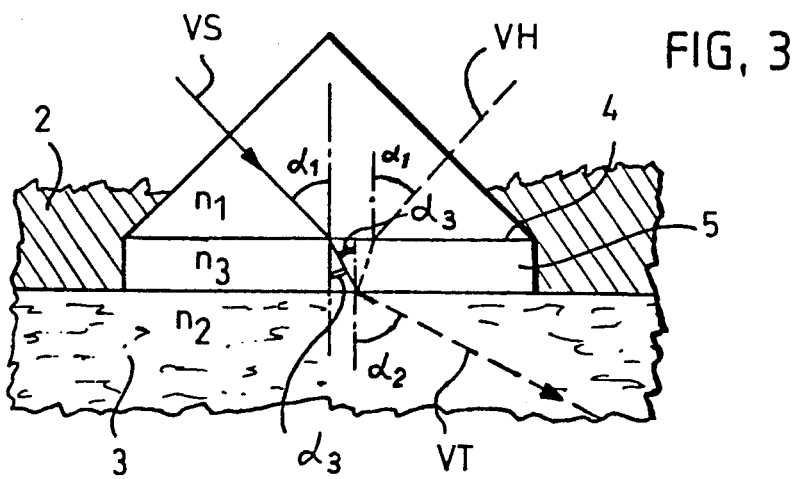

In the following the invention will be described in greater detail with the aid of an advantageous embodiment presented in the attached drawing, wherein FIG. 1 shows a principle view of the measurement principle of a measuring performed by a conventional process refractometer, FIG. 2 shows the measurement principle of FIG. 1 in a total reflection situation, i.e. when all the light beams are reflected, FIG. 3 shows the path of light in a prism according to the invention.

FIG. 1 shows the normal measurement principle of a measuring performed by a process refractometer. The prism providing an optical window for the refractometer is indicated by the reference number 1. The refractometer to which the prism 1 is fastened is indicated by the number 2. The process material to be measured in indicated by the number 3.

FIG. 1 depicts only part of the refractometer. The refractometer may be any known apparatus, e.g. Process Refractometer PR-01 manufactured by K-Patents Oy.

The refractory index of the material that the prism is manufactured from is $n_1$ and the refractory index of the material to be measured is $n_2$. The refractory index of the prism 1 is selected such that $n_1 > n_2$. When light beams VS meet the surface of the prism 1 that is in contact with the process material, i.e. an interface 4, some light beams VT pass through the interface while others VH reflect from the interface. As the light passes through the interface 4, refraction occurs such that if the incidence angle of light is $\alpha_1$ and the angle of dispart is $\alpha_2$ then $\alpha_2 > \alpha_1$. Also the equation $$n_1 \sin \alpha_1 = n_2 \sin \alpha_2$$

which can be written in the form $$\sin \alpha_1 = (n_2/n_1)\sin \alpha_2$$

holds true.

With the critical angle value $\alpha_c$ all incident light beams are refracted from the interface 4, i.e. total reflection occurs on the interface. This is shown in principle in FIG. 2. The angle $\alpha_2 = 90°$. $\sin \alpha_2$ is then 1, and when the above formula is applied, $$\sin \alpha_c = n_2/n_1.$$

The above matters and the structure and operation of a process refractometer are quite conventional techniques to one skilled in the art, wherefore they are not discussed any closer herein.

In accordance with the basic idea of the invention, an optically transparent material layer 5 is provided onto the surface of the interface 4 in contact with the process material 3, the refractory index $n_3$ of the material 5 being higher than the refractory index $n_1$ of the material that the prism 1 is manufactured from.

The solution according to the invention is shown in principle in FIG. 3. The incident light beams are indicated in FIG. 3 in the same way as in FIGS. 1 and 2, i.e. by the reference VS. The light beams passing through the interface 4 and the material layer 5 are indicated in FIG. 3 by the reference VT. The reflected light beams are indicated by the reference VH. The angles of the light beams are shown in FIG. 3 in the same manner as e.g. in FIG. 1. When the previously mentioned formula is applied in a situation shown in FIG. 3, the following equations can be written:

$$\sin \alpha_1 = (n_3/n_1)\sin \alpha_3$$

$$\sin \alpha_3 = (n_2/n_3)\sin \alpha_2.$$

By combining the two equations above, the following equation is obtained:

$$\sin \alpha_1 = (n_1/n_2)\sin \alpha_2.$$

From the above equations it can be seen that the situation does not change in respect of reflection of a light beam although the above-mentioned optically transparent material layer 5 is provided onto the surface of the prism if the dependency of the refractory index is $n_3 > n_1 > n_2$ and the material layer 5 is such that the outer surface of the layer is parallel to the interface 4. As shown in FIG. 3, when the light passes through the layer 5 only parallel displacement occurs with respect to FIG. 1.

Thus it is possible to provide a layer of any wear resistant material having small friction and low adhesive capacity onto the interface 4 of the prism if the material is selected such that it is optically transparent. An example for a suitable material is diamond material obtained e.g. by ionising carbon-containing gases and combining the carbon atoms to provide a diamond structure onto the interface 4 of the prism 1.

This enables free selection of prism material on optical criteria. The wear resistance needed is obtained by means of the above layer 5. Thus an optimal measuring situation is obtained in all circumstances.

The above embodiment of the invention is not intended to restrict the invention in any way but the invention can be modified quite freely within the scope of the claims. It is thus clear that the prism according to the invention need not necessarily be exactly as shown in the figures but other solutions are also possible.

I claim:

1. A prismatic device for use with a process refractometer to measure a condition of a process material having a refractive index, the device comprising: a prismatic body having a refractive index greater than the refractive index of the process material to be measured, and having a planar face portion; an optically transparent layer of material having a index greater than the refractive index of the prismatic body; the optically transparent material comprising a first surface bonded to the planar face portion of the prismatic body and defining a first interface therebetween, and comprising a second surface disposed for contact with the process material to be measured, a second interface being defined by the second surface and the process material to be measured.

2. A prismatic device according to claim 1, wherein the second surface of the optically transparent layer is parallel to the first interface.

3. A prismatic device according to claim 1, wherein the optically transparent layer of material has higher wear resistance than the material of the prismatic body.

4. A prismatic device according to claim 3, wherein the optically transparent layer of material comprises diamond material.

5. A prismatic device according to claim 2, wherein the optically transparent layer of material has higher wear resistance than the material of the prismatic body.

6. A prismatic device according to claim 5, wherein the optically transparent layer of material comprises diamond material.

* * * * *